US010966939B2

(12) United States Patent
Guy et al.

(10) Patent No.: US 10,966,939 B2
(45) Date of Patent: *Apr. 6, 2021

(54) USE OF CANNABINOIDS IN THE TREATMENT OF EPILEPSY

(71) Applicant: GW Research Limited, Cambridge (GB)

(72) Inventors: Geoffrey Guy, London (GB); Stephen Wright, London (GB); Orrin Devinsky, New York, NY (US)

(73) Assignee: GW Research Limited, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/911,914

(22) Filed: Jun. 25, 2020

(65) Prior Publication Data
US 2020/0323792 A1 Oct. 15, 2020

Related U.S. Application Data

(63) Continuation of application No. 16/198,141, filed on Nov. 21, 2018, now Pat. No. 10,849,860, which is a continuation of application No. 15/449,535, filed on Mar. 3, 2017, now Pat. No. 10,137,095, which is a continuation of application No. 14/881,969, filed on Oct. 13, 2015, now Pat. No. 10,111,840.

(30) Foreign Application Priority Data

Oct. 14, 2014 (GB) ..................................... 1418171

(51) Int. Cl.
A61K 31/045 (2006.01)
A61P 25/08 (2006.01)
A61K 31/05 (2006.01)
A61K 47/10 (2017.01)
A61K 9/08 (2006.01)
A61K 45/06 (2006.01)
A61K 31/352 (2006.01)

(52) U.S. Cl.
CPC ................ *A61K 31/05* (2013.01); *A61K 9/08* (2013.01); *A61K 31/352* (2013.01); *A61K 45/06* (2013.01); *A61K 47/10* (2013.01)

(58) Field of Classification Search
CPC .............................. A61K 31/045; A61P 25/08
USPC ....................................................... 514/729
See application file for complete search history.

(56) References Cited

U.S. PATENT DOCUMENTS

| 6,383,513 | B1 | 5/2002 | Watts et al. |
| 6,403,126 | B1 | 6/2002 | Webster |
| 6,949,582 | B1 | 9/2005 | Wallace |
| 8,293,786 | B2 | 10/2012 | Stinchcomb |
| 8,603,515 | B2 | 12/2013 | Whittle |
| 8,673,368 | B2 | 3/2014 | Guy et al. |
| 9,017,737 | B2 | 4/2015 | Kikuchi et al. |
| 9,023,322 | B2 | 5/2015 | Van Damme et al. |
| 9,066,920 | B2 | 6/2015 | Whalley et al. |
| 9,125,859 | B2 | 9/2015 | Whalley et al. |
| 9,095,554 | B2 | 10/2015 | Lewis et al. |
| 9,168,278 | B2 | 10/2015 | Guy et al. |
| 9,259,449 | B2 | 2/2016 | Raderman |
| 9,474,726 | B2 | 10/2016 | Guy et al. |
| 9,522,123 | B2 | 12/2016 | Whalley et al. |
| 9,949,936 | B2 | 4/2018 | Guy et al. |
| 9,949,937 | B2 | 4/2018 | Guy |
| 9,956,183 | B2 | 5/2018 | Guy |
| 9,956,184 | B2 | 5/2018 | Guy |
| 9,956,185 | B2 | 5/2018 | Guy |
| 9,956,186 | B2 | 5/2018 | Guy |
| 10,092,525 | B2 | 10/2018 | Guy et al. |
| 10,111,840 | B2 * | 10/2018 | Guy ....................... A61P 25/08 |
| 10,137,095 | B2 | 11/2018 | Guy et al. |
| 10,603,288 | B2 | 3/2020 | Guy et al. |
| 10,709,673 | B2 | 7/2020 | Guy |
| 10,709,674 | B2 | 7/2020 | Guy et al. |
| 10,849,860 | B2 | 12/2020 | Guy et al. |
| 2004/0034108 | A1 | 2/2004 | Whittle |
| 2004/0049059 | A1 | 3/2004 | Mueller |
| 2004/0110828 | A1 | 6/2004 | Chowdhury et al. |
| 2005/0042172 | A1 | 2/2005 | Whittle |
| 2005/0266108 | A1 | 12/2005 | Flockhart et al. |
| 2006/0039959 | A1 | 2/2006 | Wessling |
| 2007/0060638 | A1 | 3/2007 | Olmstead |

(Continued)

FOREIGN PATENT DOCUMENTS

CA 2737447 A1 10/2012
CA 2859934 A1 3/2016

(Continued)

OTHER PUBLICATIONS

U.S. Appl. No. 13/380,305, filed Mar. 19, 2012, Benjamin Whalley.
U.S. Appl. No. 14/579,061, filed Dec. 22, 2014, Benjamin Whalley.
U.S. Appl. No. 15/346,844, filed Nov. 9, 2016, Benjamin Whalley.
U.S. Appl. No. 16/149,983, filed Oct. 2, 2018, Benjamin Whalley.
U.S. Appl. No. 13/977,766, filed Jul. 1, 2013, Benjamin Whalley.
U.S. Appl. No. 14/345,968, filed Mar. 20, 2014, Benjamin Whalley.
U.S. Appl. No. 14/741,783, filed Jun. 17, 2015, Geoffrey Guy.
U.S. Appl. No. 15/284,766, filed Oct. 4, 2016, Geoffrey Guy.

(Continued)

*Primary Examiner* — Raymond J Henley, III
(74) *Attorney, Agent, or Firm* — Cooley LLP

(57) ABSTRACT

The present disclosure relates to the use of cannabidiol (CBD) for the treatment of atonic seizures. In particular the CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types. The disclosure further relates to the use of CBD in combination with one or more anti-epileptic drugs (AEDs).

21 Claims, 1 Drawing Sheet

(56) References Cited

U.S. PATENT DOCUMENTS

| | | |
|---|---|---|
| 2007/0099987 A1 | 5/2007 | Weiss et al. |
| 2008/0119544 A1 | 5/2008 | Guy et al. |
| 2008/0188461 A1 | 8/2008 | Guan |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0270845 A1 | 10/2012 | Bannister |
| 2013/0143894 A1 | 6/2013 | Bergstrom et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0343071 A1 | 12/2015 | Vangara et al. |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Wilkhu et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0091171 A1 | 3/2019 | Guy et al. |
| 2020/0000741 A1 | 1/2020 | Guy et al. |
| 2020/0179303 A1 | 6/2020 | Guy et al. |
| 2020/0368179 A1 | 11/2020 | Guy et al. |

FOREIGN PATENT DOCUMENTS

| | | |
|---|---|---|
| CN | 101040855 A | 9/2007 |
| CN | 103110582 A | 5/2013 |
| DE | 102012-105063 | 12/2013 |
| EP | 2448637 B1 | 5/2012 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2471565 B | 7/2012 |
| GB | 2478072 B | 12/2012 |
| GB | 2478074 B | 12/2012 |
| GB | 2492487 A | 1/2013 |
| GB | 2487712 | 10/2015 |
| GB | 2531282 | 4/2016 |
| GB | 2438682 A | 12/2017 |
| WO | WO 02/064109 A2 | 8/2002 |
| WO | WO 03/099302 A1 | 12/2003 |
| WO | WO 04/016246 A1 | 2/2004 |
| WO | WO 04/016277 A2 | 2/2004 |
| WO | WO 2006/054057 A2 | 5/2006 |
| WO | WO 2006/017892 A1 | 12/2006 |
| WO | WO 2006/133941 A2 | 12/2006 |
| WO | WO 2007/083098 A1 | 7/2007 |
| WO | WO 2007/138322 A1 | 12/2007 |
| WO | WO 2008/019146 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/021394 A2 | 12/2008 |
| WO | WO 2008/146006 A1 | 12/2008 |
| WO | WO 2009/007697 A1 | 1/2009 |
| WO | WO 2011/001169 A1 | 1/2011 |
| WO | WO 2011/121351 A1 | 10/2011 |
| WO | WO 2012/093255 A1 | 7/2012 |
| WO | WO 2013/032351 A1 | 3/2013 |
| WO | WO 2015/142501 A1 | 9/2015 |
| WO | WO 2015/184127 A2 | 12/2015 |
| WO | WO 2015/187988 A1 | 12/2015 |
| WO | WO 2015/193667 A1 | 12/2015 |
| WO | WO 2015/193668 A1 | 12/2015 |
| WO | WO 2016/059405 A1 | 4/2016 |
| WO | WO 2016/084075 A1 | 6/2016 |
| WO | WO 2016/118391 A1 | 7/2016 |
| WO | WO 2016/147186 A1 | 9/2016 |
| WO | WO 2016/022936 A1 | 11/2016 |
| WO | WO 2016/199148 A1 | 12/2016 |
| WO | WO 2017/168138 A1 | 10/2017 |
| WO | WO 2018/002636 A1 | 1/2018 |
| WO | WO 2018/002637 A1 | 1/2018 |
| WO | WO 2018/037203 A1 | 3/2018 |

OTHER PUBLICATIONS

U.S. Appl. No. 15/449,084, filed Mar. 3, 2017, Geoffrey Guy.
U.S. Appl. No. 15/449,124, filed Mar. 3, 2017, Geoffrey Guy.
U.S. Appl. No. 15/449,185, filed Mar. 3, 2017, Geoffrey Guy.
U.S. Appl. No. 15/449,204, filed Mar. 3, 2017, Geoffrey Guy.
U.S. Appl. No. 15/449,177, filed Mar. 3, 2017, Geoffrey Guy.
U.S. Appl. No. 15/948,412, filed Apr. 9, 2018, Geoffrey Guy.
U.S. Appl. No. 14/881,954, filed Oct. 13, 2015, Geoffrey Guy.
U.S. Appl. No. 14/881,969, filed Oct. 13, 2015, Geoffrey Guy.
U.S. Appl. No. 15/449,402, filed Mar. 3, 2017, Geoffrey Guy.
U.S. Appl. No. 15/449,535, filed Mar. 3, 2017, Geoffrey Guy.
U.S. Appl. No. 16/198,141, filed Nov. 21, 2018, Geoffrey Guy.
U.S. Appl. No. 14/741,829, filed Jun. 17, 2015, Geoffrey Guy.
U.S. Appl. No. 15/183,947, filed Jun. 16, 2015, Geoffrey Guy.
U.S. Appl. No. 15/519,233, filed Apr. 14, 2017, Geoffrey Guy.
U.S. Appl. No. 15/519,244, filed Apr. 14, 2017, Geoffrey Guy.
U.S. Appl. No. 15/640,033, filed Jun. 30, 2017, Jitinder Walkhu.
U.S. Appl. No. 15/751,563, filed Feb. 9, 2018, Colin Stott.
U.S. Appl. No. 16/090,039, filed Sep. 28, 2018, Geoffrey Guy.
U.S. Appl. No. 16/314,583, filed Dec. 31, 2018, Stephen Wright.
U.S. Appl. No. 16/314,569, filed Dec. 31, 2018, Harshit Shah.
U.S. Appl. No. 16/328,209, filed Feb. 25, 2019, Colin Stott.
U.S. Appl. No. 16/467,639, filed Jun. 7, 2019, Guy.
[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.
[No Author Listed] GW Pharmaceuticals Provides Update on Orphan Program in Childhood Epilepsy for Epidiolex, GW. Pharm. Available online Nov. 14, 2013, Retrieved Feb. 10, 2017.
[No Author Listed] "What are the Highest CBD Strains?"accessed Feb. 16, 2017, published Oct. 15, 2014.
[No Author Listed] "Cannabidiol Therapy for Aicardi Syndrome" Aug. 2014.

(56) References Cited

OTHER PUBLICATIONS

[No Author Listed] "Convulsive Disorders and Their Interference with Diiving," Medicos., Retrieved Feb. 10, 2017, Retrieved from internet: URL https://www.medicosporlaseguridadvial.com/en/clinical-subjects/neurologic-diseases/convulsive-disorders-and-their-interference-with-driving/, 2014.
[No Author Listed] Cannabinoid. Wikipedia. Retrieved on Jul. 9, 2015 from https://en. wikipedia.org/wiki/Cannabinoid.
[No Author Listed] Estimating the Maximum Safe Starting Dose in Initial Clinical Trials for Therapeutics in Adult Healthy Volunteers. FDA Guidance for Industry, Jul. 2005.
[No Author Listed] GW Pharmaceuticals Announces Epidiolex Receives Fast Track Designation from FDA for the Treatment of Dravet Syndrome. GW Pharmaceuticals Press Release dated Jun. 6, 2014.
Annex to the Communication—Opposition for Application No. 10734541.5, dated Jan. 28, 2016.
Arzimanoglou et al. Epileptic Disord. 2011, 13, S3-S13 (Year: 2011).
Brown et al., Child Neurology Foundation, "LGS" (Lennox-Gastaut Syndrome), available at http://www.childneurologyfoundation.org/disorders/lgs-lennox-gastaut-syndrome.
"Cannabidiols: Potential Use in Epilepsy & Other Neurological Disorders." Cannabidol Conference at NYU School of Medicine, Oct. 2013. NYU Langone Health. Retreived from the Internet Nov. 2019.<URL: http://faces.med.nyu.edu/research-education/cannabidiol-conference>.
Charlotte's Web [ online], "Whole-Plant Cannabinoids Outperform Single Molecule Compounds,"CWHemp.com, Jan. 11, 2017, retrieved on Jun. 16, 2017, URL https://www.cwhemp.com/blog/whole-plant-cw-hemp-cannabinoids.
Chiu et al., "The Influence of Cannabidiol and □ 9-Tetrahydrocannabinol on Cobalt Epilepsy in Rats," Epilepsia., 1979, 20:365-375.
Cilio, Maria Roberta, M.D., Ph.D. of the Pediatric Epilepsy and Clinical Neurophysiology for the University of California, San Francisco presents her talk on "CBD in Children with Treatment-Resistant Epilepsies: Planned Trials in Dravet and Lennox-Gastaut Syndromes," at NYU School of Medicine's Cannabidiol Conference (Oct. 4, 2013). Video published online. <http://faces.med.nyu.edu/research-education/cannabidiol-conference>.
Combined Search and Examination Report dated Jan. 4, 2012 for Application No. GB: 1116789.7.
Combined Search and Examination Report dated Mar. 25, 2011 for Application No. GB: 1100043.7.
Combined Search and Examination Report dated Sep. 5, 2014 for Application No. GB 1414813.4.
Combined Search and Examination Report Under Sections 17 and 18 (3) for International Application No. GB1121919.3, dated Feb. 29, 2012.
Combined Search and Examination Report Under Sections 17 and 18 (3) for International Application No. GB 1410771.8, dated Feb. 27, 2018.
Combined Search and Examination Report Under Sections 17 and 18 (3) for International Application No. GB 1418166.3, dated Jul. 2, 2015.
Combined Search and Examination Report Under Sections 17 and 18 (3) for International Application No. GB 1418170.5, dated Jul. 2, 2015.
Combined Search and Examination Report Under Sections 17 and 18 (3) for International Application No. GB 1418171.3, dated Jun. 29, 2015.
Combined Search and Examination Report Under Sections 17 and 18 (3) for International Application No. GB 1506550.1, dated Feb. 5, 2016.
Communication of a Notice of Opposition for Application No. 107342541.5 dated Dec. 17, 2014.
Communication Pursuant to Article 94(3) EPC in European Patent Application No. 10734541.5, dated Oct. 23, 2012.

Consroe et al., "Controlled clinical trial of cannabidiol in Huntington's Disease," Pharmacology Biochemistry & Behavior, 1991, 40:701-708.
Crespel et al., "Lennox-Gastaut Syndrome," Chapter 14, in Epileptic Syndromes in Infancy, Childhood, and Adolescence, 5th Edition, ed. M. Bureau, et al., pp. 189-216.
Decision in IPR2017-00503 dated Jul. 7, 2017.
Decision in Opposition proceedings (Art. 101(3)(a) and 106(2) EPC in European Patent Application No. EP2448637, dated Dec. 15, 2016.
Declaration of Professor Anthony G.Marson in the Inter Partes Review of U.S. Pat. No. 9,066,920, Dated Dec. 13, 2016.
Declaration of Professor Leslie Benet in the Inter Partes Review of U.S. Pat. No. 9,066,920, Dated Nov. 22, 2016.
Declaration of Professor H. Steve White in the Inter Partes Review of U.S. Pat. No. 9,066,920, Dated Oct. 24, 2017.
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edu/research-education/cannabidiol-conference>.
Di Marzo, Vincenzo, Ph.D. of the Endocannabinoid Research Group Istituto di Chimica Biomolecolare, Consiglio Nazionale delle Ricerche, Pozzuoli, Napoli, Italy presents his talk on "Cannabinoid Pharmacology & Mechanism of Action," at NYU School of Medicine's Cannabidiol Conference (Oct. 4, 2013). Video published online. <http://faces.med.nyu.edu/research-education/cannabidiol-conference>.
Dravet, The core Dravet syndrome phenotype. Epilepsia.52 Suppl 2:3-9. doi: 10.1111/j.1528-1167.2011.02994.x. (Year: 2011).
Drugs of the Future, 39(1): 49-56, Jan. 2014 notes Orphan Drug designation for CBD for Lennox-Gastaut Syndrome.
Engel, Report of the ILAE classification core group. Epilepsia. Sep. 2006;47(9): 1558-68.
Etienne de Meijer, "The Chemical Phenotypes (Chemotypes) of Cannabis," Chapter 5, Handbook of Cannabis, ed. Roger G. Pertwee, pp. 89-110 (2014).
Ex parte Edelstam, Appeal No. 2016/006358, mail date Jun. 21, 2017 (Year: 2017).
Ex parte Miller, Appeal 2009-011751, mail date Jul. 8, 2010 (Year: 2010).
Examination Report dated Mar. 18, 2014 for Application No. GB1100043.7.
Expert Statement of Vincenzo Di Marzo for Application No. EP10734541.5 dated Sep. 9, 2016.
Expert Statement of Professor Benjamin J. Whalley for Application No. EP10734541.5 dated Sep. 9, 2016.
Expert Statement of Professor Anthony G. Marson for for Application No. EP10734541.5.
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online. <http://faces.med.nyu.edu/research-education/cannabidiol-conference>.
Friedman, Daniel, M.D. Assistant Professor of Neurology at the NYU Comprehensive Epilepsy Center presents his talk on "Pharmacology of CBD in Humans," at NYU School of Medicine's Cannabidiol Conference (Oct. 4, 2013). Video published online. <http://faces.med.nyu.edu/research-education/cannabidiol-conference>.
Gardner [online], "Comes Now Epidiolex (FDA Approves IND Studies of CBD)," BeyondTHC.com, Oct. 22, 2013, retrieved on Jan. 31, 2018, URL http://www.beyondthc.com/comes-now-epidiolex-fda-approves-ind-studies-of-cbd.
Guerrini et al., "Lamotrigine and Seizure Aggravation in Severe Myoclonic Epilepsy," Epilepsia, 39(5):508-512, 1998.
Goodman & Gilman, The Pharmacological Basis of Therapeutics (Brunton, Laurence L.; Lazo, John S.; Parker, Keith, eds. (2006); (I Ith ed.), New York: McGraw-Hill. ISBN 0-07-142280-3); Chapter 19, Pharmacotherapy of the Epilepsies.
GWPhann [online], "GW Pharmaceuticals Announces Epidiolex(R) Receives Fast Track Designation from FD A for the Treatment of Dravet Syndrome," GW Pharmaceuticals Press Release, Jun. 6,

(56) References Cited

OTHER PUBLICATIONS 2014, retrieved on Mar. 1, 2017, URL https://www.gwphann.com/about-us/news/gw-pharmaceuticals-announces-epidiolex%C2%AE-receives-fast-track-designation-fda-treatment.

*Insys Development Comp any, Inc. v. GW Pharma Limited and Otsuka Pharmaceutical Co., Ltd.*, Petitioner's Reply to Response in IPR2017-00503, U.S. Pat. No. 9,066,920, dated Jan. 19, 2018.

International Preliminary Report on Patentability in International Application No. PCT/GB2010/051066, dated May 5, 2011.

International Preliminary Report on Patentabiliiy for Application No. PCT/GB2015/053030, dated Apr. 18, 2017.

International Preliminary Report on Patentability for Application No. PCT/GB2012/052284, dated Mar. 29, 2014.

International Search Report and Written Opinion for Application No. PCT/GB2015/051775, dated Dec. 23, 2015.

International Search Report and Written Opinion for Application No. PCT/GB2015/051066, dated Jan. 1, 2012.

International Search Report and Written Opinion for Application No. PCT/GB2011/050649, dated Sep. 30, 2012.

International Search Report and Written Opinion dated Nov. 16, 2012 for Application No. PCT/GB2012/052284, dated Mar. 29, 2014.

International Search Report in International Application No. PCT/GB2010/051066, dated Jan. 6, 2011.

International Search Report in International Application No. PCT/GB2012/050002, dated Jul. 12, 2012.

Jones et al. [online], Info & Metrics / Article Information,"Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.

Jutras-Aswad, Didier, M.D., M.S. of the Department of Psychiatry for the University of Montreal presents his talk on "CBD in Animal Models and Human Trials of Opiate Abuse," at NYU School of Medicine's Cannabidiol Conference (Oct. 4, 2013). Video published online. <http://faces.med.nyu.edu/research-education/cannabidiol-conference>.

Karler, et al. "The anticonvulsant activity of cannabidiol and cannabinol." Life Sci. De. 1, 1973;13(11):1527-31. doi: 10.1016/0024-3205(73)90141-0.

Katz, Russell ("Rusty"), M.D. former Director of the Division of Neurology Products at the FDA presents his talk on "Dravet and Lennox-Gastaut Syndromes: The Orphan Drug Process," at NYU School of Medicine's Cannabidiol Conference (Oct. 4, 2013). Video published online. <http://faces.med.nyu.edu/research-education/cannabidiol-conference>.

Khan et al., Muheet-e-Azam, vol. II. 1887: 147. Persian. Exhibit 1.

Kwan et al., Definition of drug resistant epilepsy: consensus proposal by the ad hoc Task Force of the ILAE Commission on Therapeutic Strategies. Epilepsia. Jun. 2010;51(6):1069-77. doi:10.1111/j.1528-1167.2009.02397.x. Epub Nov. 3, 2009. Erratum in: Epilepsia. Sep. 2010;51(9): 1922.

LeafScience.com [online], "What are the Highest CBD Strains?" Oct. 15, 2014, retrieved on Feb. 16, 2017, URL www.leafscience.com/2014/10/15/highest-cbd-strains/.

Manno. "Status Epilepticus: Current Treatment Strategies," The Neurohospitalist. Jan. 2011, 1(1):23-31.

Mechoulam et al., "Cannabidiol: An Overview of Some Pharmacological Aspects," J Clin Pharmacol, 2002, 42:11S-19S.

Mechoulam et al., Toward drugs derived from cannabis. Naturwissenschaften. Apr. 1978;65(4):174-9.

Models of Chemically-Induced Acute Seizures 127-152, 2006.

Notice of Allowance in U.S. Appl. No. 13/380,305, dated Dec. 10, 2014.

Notice of Allowance in U.S. Appl. No. 13/380,305, dated Mar. 19, 2015.

Notice of Appeal in European Patent No. EP2448637, dated Feb. 14, 2017.

Notice of Opposition to a Europearn Patent No. EP2448637, Dated Dec. 5, 2014.

Office Action in U.S. Appl. No. 13/380,305, dated Aug. 25, 2014.

Opponent Response to the Preliminary Opinion of the Opposition Division in European Patent No. EP2448637, dated Jun. 23, 2016.

Opponent Response dated to Sep. 9, Preliminary 2016, 25 Opinion pages of the Opposition Division in European Patent No. EP2448637, dated Sep. 9, 2016.

Opponent Response to the Written Submissions in European Patent No. EP2448637, dated Oct. 12, 2016.

Opponent Response to the Written Submissions in European Patent No. EP2448637, dated Oct. 20, 2016.

Opponent Response to the Written Submissions in European Patent No. EP2448637, dated Nov. 4, 2016.

Patent Owners' Preliminary Response for IPR2017-00503 dated Apr. 11, 2017.

PCT International Preliminary Report on Patentability in International Appln. No. PCT/US2017/050868, dated Jun. 18, 2019.

PCT International Search Report and Written Opinion in International Appln. No. PCT/US2017/050868, dated Jun. 21, 2018.

Petition for Inter Partes Review U.S. Pat. No. 9,066,920 dates Dec. 16, 2016.

Petitioner's Reply to Patent Owner's Response in Inter Partes Review No. IPR2017-00503, filed Jan. 19, 2018.

Resstel et al., 5-HT1A receptors are involved in the cannabidiol-induced attenuation of behavioural and cardiovascular responses to acute restraint stress in rats. Br J Pharmacol. Jan. 2009;156(1): 181-8.

Reply of the Patent Proprietor to the Notice(s) of Opposition in European Patent No. 2448637, dated May 28, 2015, 12 pages.

Reply to Communication from the examining Division in Eurppean Patent Application No. 10734541.5 dated Feb. 15, 2013, 54 pages.

Reply to EPO Communication in European Patent No. EP2448637, dated Nov. 2, 2016, 45 pages.

Reply to Opponent's Written Submission in European Patent No. EP2448637, dated Nov. 4, 2016, 13 pages.

Reply to Opponent's Written Submission in European Patent No. EP2448637, dated Oct. 18, 2016, 5 pages.

Reply to Preliminary Opinion and Opponent's Observations in European Patent No. EP2448637, dated Sep. 9, 2016, 65 pages.

Request for Continued Examination with the Amendment and Information Disclosure Statement in U.S. Appl. No. 13/380,305, filed Mar. 2, 2015, 3 pages.

Rohrback, Brian G., Ph.D, MBA President of Infometrix, Inc. presents his talk on "Assays of Cannabinoids," at NYU School of Medicine's Cannabidiol Conference (Oct. 4, 2013). Video published online. <http://faces.med.nyu.edu/research-education/cannabidiol-conference>.

Rosenberg et al., "Cannabinoids and Epilepsy," Neurotherapeutics, Oct. 2015, 12(4): 747-768.

Silva, R. et al. Can J. Neurol. Sci. 2006 vol. 33 pp. 783-86.

Statement of Opposition for EP10734541.5, mailed Dec. 5, 2014.

Swann et al., The effects of seizures on the connectivity and circuitry of the developing brain. Ment Retard Dev Disabil Res Rev. 2004; 10(2):96-100.

Stafstrom et al., "Models of Pediatric Epilepsies: Strategies and Opportunities," Epilepsia, vol. 47, No. 8, 2006.

Statement of Grounds of Appeal for European Application No. 10734541.5 in the name of GW Pharma and Otsuka Pharmaceutical Co. Limited Appellant/Opponent: Insys Therapeutics Inc., dated Apr. 21, 2017.

Statement of Grounds of Appeal for European Application No. 10734541.5 on behalf of the Proprietors: GW Pharma Limited and Otsuka Pharmaceutical CO Limited, dated Apr. 12, 2017.

Tanya Lewis, Mystery Mechanisms, The Scientist Magazine, Jul. 29 2016.

Transcript of Dr. H. Steven White's deposition, dated Dec. 29, 2017.

Third Party Observations for Application No. AU20 1 2314128, mailed Mar. 19, 2015.

Third Party Observations for Application No. EP10734541.5, mailed Apr. 3, 2017.

Third Party Observations for Application No. EP1712658.1, mailed Nov. 22, 2013.

Wallace et al., "Pharmacotherapy forDravet Syndrome," Pediatr. Drugs, 18:197-208 (2016).

(56) References Cited

OTHER PUBLICATIONS

Wallace et al., Assessment of the role of CB 1 receptors in cannabinoid anticonvulsant effects. Eur J Pharmacol. Sep. 28, 2001;428(1):51-7.

Whalley, Benjamin J. Ph.D. of the University of Reading presents his talk on "Cannabis and Epilepsy: Cannabidiol (CBD) and Cannabidavarin (CBDV) in Preclinical Models of Seizure and Epilepsy," at NYU School of Medicine's Cannabidiol Conference (Oct. 4, 2013). Video published online. <http://faces.med.nyu.edu/research-education/cannabidiol-conference>.

"When to Expect Results from CW Hemp Oil", downloaded Sep. 5, 2017, https://www.cwhemp.com/blog/expecting-results-from-hemp.

Wikipedia.org [online], "Cannabinoid," Wikipedia, Apr. 2003, retrieved on Mar. 1, 2017, URL <https://en.wikipedia.org/wiki/Cannabinoid>.

* cited by examiner

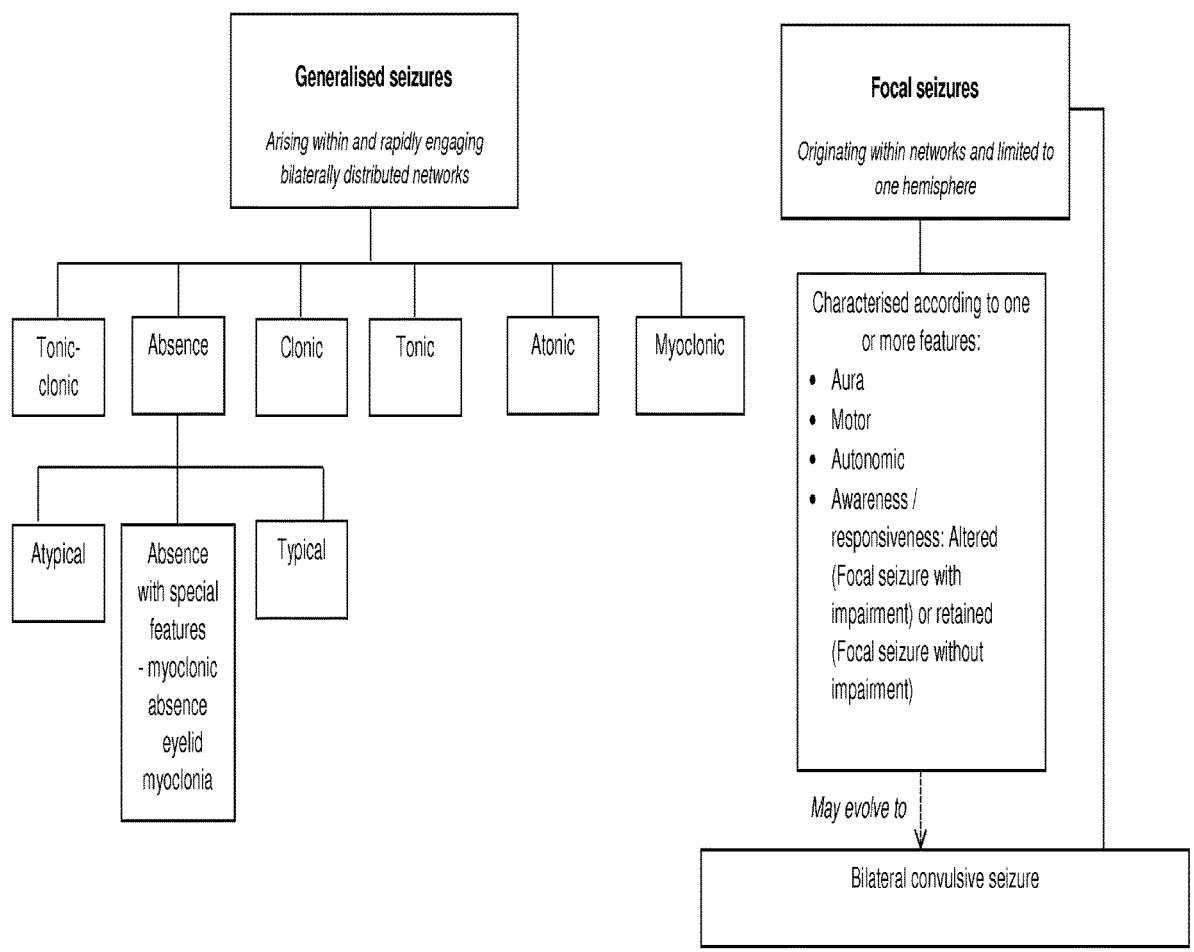

USE OF CANNABINOIDS IN THE TREATMENT OF EPILEPSY

CROSS-REFERENCE TO RELATED APPLICATIONS

This application is a continuation of U.S. patent application Ser. No. 16/198,141, filed Nov. 21, 2018, now U.S. Pat. No. 10,849,860, which is a continuation of U.S. patent application Ser. No. 15/449,535, filed Mar. 3, 2017, now U.S. Pat. No. 10,137,095, which is a continuation of Ser. No. 14/881,969, filed Oct. 13, 2015, now U.S. Pat. No. 10,111,840 which claims priority to GB 1418171.3, filed Oct. 14, 2014. Each of these applications is incorporated herein by reference in its entirety.

FIELD OF THE INVENTION

The present invention relates to the use of cannabidiol (CBD) in the treatment of atonic seizures. In one embodiment the patients suffering from atonic seizures are children and young adults. CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types.

In these patients treatment with CBD reduced the occurrence of atonic seizures by greater than 50% in a large proportion, namely 63%, of patients. This was surprising given that the proportion of patients benefitting from a greater than 50% reduction in total seizures was significantly less, (46%), in all subjects treated.

Preferably the CBD used is in the form of a highly purified extract of cannabis such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD may be given concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal. In addition the term "simple partial seizure" has been replaced by the term "focal seizure where awareness/responsiveness is not impaired" and the term "complex partial seizure" has been replaced by the term "focal seizure where awareness/consciousness is impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace Secondary Generalized Seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Atonic seizures involve the loss of muscle tone, causing the person to fall to the ground. These are sometimes called 'drop attacks' and are usually brief (less than 15 seconds). Atonic seizures can occur without warning while standing, sitting and walking and the patient often suffers from trauma due to falling.

Atonic seizures are often associated with Lennox-Gastaut Syndrome but also occur, and may be symptomatic of other types of epileptic syndromes including: Tuberous Sclerosis Complex; Dravet Syndrome; Doose Syndrome; Aicardi syndrome; CDKL5 and Dup15q.

Epileptic syndromes often present with many different types of seizure and identifying the types of seizure that a patient is suffering from is important as many of the standard AED's are targeted to treat or are only effective against a given seizure type/sub-type.

One such childhood epilepsy syndrome is Lennox-Gastaut syndrome. Lennox-Gastaut syndrome is a severe form of epilepsy. Seizures usually begin before the age of 4. Seizure types, which vary among patients, include tonic (stiffening of the body, upward deviation of the eyes, dilation of the pupils, and altered respiratory patterns), atonic (brief loss of muscle tone and consciousness, causing abrupt falls), atypical absence (staring spells), and myoclonic (sudden muscle jerks). There may be periods of frequent seizures mixed with brief, relatively seizure-free periods.

Most children with Lennox-Gastaut syndrome experience some degree of impaired intellectual functioning or information processing, along with developmental delays, and behavioural disturbances.

Lennox-Gastaut syndrome can be caused by brain malformations, perinatal asphyxia, severe head injury, central nervous system infection and inherited degenerative or metabolic conditions. In 30-35 percent of cases, no cause can be found.

The first line treatment for atonic seizures, including the treatment of atonic seizures in patients with Lennox-Gastaut syndrome usually comprises a broad spectrum AED, such as sodium valproate often in combination with lamotrigine. Other AED that may be considered include rufinamide, felbamate, clobazam and topiramate.

AED such as carbamezapine, gabapentin, oxcarbazepine, pregabalin, tiagabineor and vigabatrin are contra-indicated in atonic seizures.

Common AED defined by their mechanisms of action are described in the following tables:

TABLE 1

Examples of narrow spectrum AED

| Narrow-spectrum AED | Mechanism | Indication |
|---|---|---|
| Phenytoin | Sodium channel | Complex partial<br>Tonic-clonic |
| Phenobarbital | GABA/Calcium channel | Partial seizures<br>Tonic-clonic |
| Carbamazepine | Sodium channel | Partial seizures<br>Tonic-clonic<br>Mixed seizures |
| Oxcarbazepine | Sodium channel | Partial seizures<br>Tonic-clonic<br>Mixed seizures |
| Gabapentin | Calcium channel | Partial seizures<br>Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures<br>Partial seizures<br>Infantile spasms due to West syndrome |

TABLE 2

Examples of broad spectrum AED

| Broad-spectrum AED | Mechanism | Indication |
|---|---|---|
| Valproic acid | GABA/Sodium channel | First-line treatment for tonic-clonic seizures, absence seizures and myoclonic seizures<br>Second-line treatment for partial seizures and infantile spasms.<br>Intravenous use in status epilepticus |
| Lamotrigine | Sodium channel | Partial seizures<br>Tonic-clonic<br>Seizures associated with Lennox-Gastaut syndrome |
| Topiramate | GABA/Sodium channel | Seizures associated with Lennox-Gastaut syndrome |
| Zonisamide | GABA/Calcium/Sodium channel | Adjunctive therapy in adults with partial-onset seizures<br>Infantile spasm<br>Mixed seizure<br>Lennox-Gastaut syndrome<br>Myoclonic<br>Generalised tonic-clonic seizure |
| Levetiracetam | Calcium channel | Partial seizures<br>Adjunctive therapy for partial, myoclonic and tonic-clonic seizures |
| Clonazepam | GABA | Typical and atypical absences<br>Infantile myoclonic<br>Myoclonic seizures<br>Akinetic seizures<br>Atonic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
|---|---|---|
| Clobazam | GABA | Adjunctive therapy in complex partial seizures<br>Status epilepticus<br>Myoclonic<br>Myoclonic-absent<br>Simple partial<br>Complex partial<br>Absence seizures<br>Lennox-Gastaut syndrome |
| Stiripentol | GABA | Severe myoclonic epilepsy in infancy (Dravet syndrome) |

From these tables it can be seen that there is only one drug currently approved for use in the treatment of atonic seizures, namely clonazepam. This medication works by the GABA mechanism.

Over the past forty years there have been a number of animal and human studies on the use of the non-psychoactive cannabinoid cannabidiol (CBD) to treat seizures.

A study in 1978 provided 200 mg/day of pure CBD to four adult patients, two of the four patients became seizure free, whereas in the remainder, seizure frequency was unchanged (Mechoulam and Carlini, 1978).

Cunha et al. reported that administration of CBD to eight adult patients with generalized epilepsy resulted in a marked reduction of seizures in 4 of the patients (Cunha et al., 1980)

and Consroe et al., (1982) determined that CBD was able to prevent seizures in mice after administration of pro-convulsant drugs or an electric current.

In contrast to the studies described above, an open label study reported that 200 mg/day of pure CBD was ineffective in controlling seizures in twelve institutionalized adult patients (Ames and Cridland, 1986).

All of the studies described above focused on the treating subjects suffering from generalised epilepsy and did not look at the treatment of specific seizure sub-types.

More recently, WO 2011/001169 describes the use of CBD in the treatment of focal seizures, WO 2012/093255 describes the use of CBD in combination with standard anti-epileptic drugs in the treatment of epilepsy and WO 2013/045891 describes a composition comprising CBD and CBDV for use in the treatment of epilepsy.

In November 2013 the company GW Pharmaceuticals made a press release to state that they were intending to treat Dravet Syndrome with CBD as it had received orphan drug designation. The company made a further press release in February 2014 that that they were intending to treat Lennox-Gastaut Syndrome with CBD as it had also received orphan drug designation.

Again the rationale was to treat a disease as opposed to the type of seizure that the subject experienced.

It has additionally been suggested that cannabis which is enriched in CBD may be efficacious in the treatment of epilepsy. A case study of a child with Lennox-Gastaut syndrome showed improvement in seizure frequency after treatment with CBD in an oily solution was reported in 2005 (Pelliccia et al. 2005).

Porter and Jacobson (2013) report on a parent survey conducted via a Facebook group which explored the use of cannabis which was enriched with CBD in children with treatment-resistant epilepsy. It was found that sixteen of the 19 parents surveyed reported an improvement in their child's epilepsy. The children surveyed for this paper were all taking cannabis that was purported to contain CBD in a high concentration although the amount of CBD present and the other constituents including THC were not known for many of the cases. Indeed, whilst CBD levels ranged from 0.5 to 28.6 mg/kg/day (in those extracts tested), THC levels as high as 0.8 mg/kg/day were reported. Providing children with TRE with a cannabis extract that comprises THC, which has been described as a pro-convulsant (Consroe et al., 1977), at a potentially psychoactive dose of 0.8 mg/kg/day, is a concern.

In addition a paper published in June 2014 describes the use of a high-CBD strain to treat a patient with Dravet Syndrome; the patient's seizure frequency was stated to be reduced by the treatment (Maa et al. 2014).

A document published after the priority application was filed discloses the use of CBD in the treatment of refractory epilepsy in the treatment of Tuberous Sclerosis Complex in patients having focal onset seizures (Geffrey et al., 2014).

Whilst the potential of cannabis and the cannabinoids, including CBD, to treat epilepsy has been rekindled, to date there has been little in the way of real data to support its efficacy in patients.

The applicant has found that CBD shows significant efficacy in reducing atonic seizures, by greater than 50% in a large proportion, namely 63%, of patients. By way of comparison the proportion of patients benefitting from a greater than 50% reduction in total seizures was significantly less, (46%), in all subjects treated.

It is additionally worth noting that the patients being treated were treatment resistant to existing AED and so consequently these figures are even the more remarkable.

BRIEF SUMMARY OF THE DISCLOSURE

In accordance with a first aspect of the present invention there is provided cannabidiol (CBD) for use in the treatment of atonic seizures.

Preferably the atonic seizures are treatment-resistant.

Preferably the atonic seizures associated with Lennox-Gastaut Syndrome; Tuberous Sclerosis Complex; Dravet Syndrome; Doose Syndrome; Aicardi syndrome, CDKL5 or Dup15q.

In one embodiment the CBD is for use in combination with one or more concomitant anti-epileptic drugs (AED).

In a further embodiment the CBD is present as a highly purified extract of cannabis which comprises at least 95% (w/w) CBD, more preferably 98% (w/w) CBD. Preferably the extract comprises less than 0.15% THC. More preferably the extract further comprises up to 1% CBDV.

In an alternative embodiment the wherein the CBD is present as a synthetic compound.

In a further embodiment of the invention the one or more AED is selected from the group consisting of: clobazam; clonazepam, levetiracetam; topiramate; stiripentol; phenobarbital; lacsamide; valproic acid; zonisamide; perampanel; and fosphenytoin.

Preferably the number of different anti-epileptic drugs that are used in combination with the CBD is reduced. Alternatively the dose of the one or more anti-epileptic drugs that are used in combination with the CBD is reduced.

Preferably the dose of CBD is greater than 5 mg/kg/day.

In accordance with a second aspect of the present invention there is provided a method of treating atonic seizures comprising administering cannabidiol (CBD) to a subject.

In accordance with a third aspect of the present invention there is provided a composition for use in the treatment of atonic seizures characterised by atonic seizures comprising cannabidiol (CBD), a solvent, a co-solvent, a sweetener, and a flavouring.

Preferably the solvent is sesame oil, the co-solvent is ethanol, the sweetener is sucralose, the flavouring is strawberry flavour and the CBD is present at a concentration of between 25/mg/ml and 100 mg/ml.

More preferably the composition comprises cannabidiol (CBD) at a concentration of between 25 to 100 mg/ml, ethanol at a concentration of 79 mg/ml, sucralose at a concentration of 0.5 mg/ml, strawberry flavouring at a concentration of 0.2 mg/ml and sesame q.s. to 1.0 ml.

BRIEF DESCRIPTION OF THE DRAWINGS

FIG. 1 shows the ILEA 2010 proposal for revised terminology for organization of seizures and epilepsies.

DEFINITIONS

Definitions of some of the terms used to describe the invention are detailed below:

The cannabinoids described in the present application are listed below along with their standard abbreviations.

TABLE 4

Cannabinoids and their abbreviations

| | | |
|---|---|---|
| CBD | Cannabidiol | [structure] |
| CBDA | Cannabidiolic acid | [structure] |
| CBDV | Cannabidivarin | [structure] |
| CBDVA | Cannabidivarinic acid | [structure] |
| THC | Tetrahydrocannabinol | [structure] |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; Aicardi syndrome; CDKL5 mutation; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

"Atonic Seizures" are defined as a convulsive type of epileptic seizure which causes the muscles to relax and the patient to flop or fall.

"Mixed seizures" are defined as the existence of both generalised and focal seizures in the same patient.

The terms "50% responder" and "50% reduction in seizure" are both terms used in clinical studies. In the present application the terms define the percentage of subjects that experienced a greater than or equal to 50% reduction in the number of seizures during treatment with CBD in comparison to the number experienced during the baseline period before the CBD was administered.

DETAILED DESCRIPTION

Preparation of Highly Purified CBD Extract

The following describes the production of the highly-purified (>98% w/w) cannabidiol extract which has a known and constant composition which was used for the expanded access trials described in Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 5 below.

TABLE 5

CBD Specification

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| Other Cannabinoids: | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT—Not more than

The purity of the CBD drug substance achieved is greater than 98%. The other cannabinoids which may occur in the extract are: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally, furthermore during purification the stereochemistry of CBD is not affected.

Production of the Intermediate

An overview of the steps to produce a botanical extract, the intermediate, are as follows:
1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS) which was used for crystallisation to produce the test material.

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS.

Production of the Drug Substance

The manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis. The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sucralose and flavouring. Two product strengths are available to allow dose titration across a wide dose range.

The 25 mg/ml solution is appropriate at lower doses and the 100 mg/ml solution at higher doses.

The drug product formulation is as described in Table 6 below:

TABLE 6

Drug Product specification

| Component | Qualitative Composition | Function | Reference to Quality Standard |
|---|---|---|---|
| Cannabidiol (CBD) | 25 mg/ml or 100 mg/ml | Active | In-house |
| Anhydrous ethanol | 79.0 mg/ml* | Excipient | Ph. Eur. |
| Sucralose | 0.5 mg/ml | Sweetener | In-house |
| Strawberry flavouring | 0.2 mg/ml | Flavouring | In-house |
| Sesame oil | q.s to 1.0 ml | Excipient | Ph. Eur. |

The drug substance, CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 6 by an amount of up to 10%.

Example 1 below describes the use of a highly purified cannabis extract comprising cannabidiol (CBD) in an expanded access treatment program in children with TRE.

Example 1: Efficacy of Cannabidiol Reducing Atonic Seizures in Children and Young Adults with Intractable Epilepsy Materials and Methods Of 137 children and young adults with severe, childhood onset treatment-resistant epilepsy (TRE), twenty-seven suffered from epilepsy that was characterised by atonic seizures. These subjects were tested with a highly purified extract of cannabidiol (CBD) obtained from a cannabis plant. All subjects presented with atonic type seizures, often in addition to other seizures. The participants in the study were part of an expanded access compassionate use program for CBD.

The epileptic syndromes that these patients suffered from were as follows: Lennox-Gastaut Syndrome; Tuberous Sclerosis Complex; Dravet Syndrome; Doose Syndrome; Aicardi syndrome, CDKL5 and Dup15q.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after 4 weeks of CBD therapy.

All patients were taking at least two concomitant anti-epileptic drugs. These included clobazam; levetiracetam; topiramate; stiripentol; phenobarbital; lacsamide; valproic acid; zonisamide. The average number of concomitant anti-epileptic drugs being taken was 2.7. The majority took either clobazam and/or valproic acid.

Results

There were 27 children and young adult patients all of whom suffered from atonic seizures received treatment with CBD for at least 12 weeks.

A summary of the 50% responders, based on 12 weeks of treatment are summarized in Table 7 below.

TABLE 7

Summary of 50% responders after 12 weeks of treatment for atonic seizures

|  | Atonic seizures (n = 27) | Total seizures (n = 137) |
| --- | --- | --- |
| >50% reduction in seizures | 63% (n = 17) | 46% (n = 63) |
| <50% reduction in seizures | 37% (n = 10) | 54% (n = 74) |

Table 7 shows that after 3 months of therapy, a remarkable 63% of patients had an equal to or greater than >50% reduction in atonic seizures, these data infer that the CBD is very effective at reducing this type of seizure.

CONCLUSIONS

These data indicate that CBD significantly reduces the number of atonic seizures in a high proportion of patients that do not respond well to existing AED.

It was surprising that in this group of patients which are treatment-resistant such a high number were able to gain an effect. The fact that nearly two thirds of the patients (63%) benefitted from at least a fifty percent reduction in the number of atonic seizures that they suffered from was remarkable.

Furthermore when these data are compared to the other sub-types of generalised seizure, it can clearly be seen that CBD was able to selectively reduce the occurrence of atonic seizures. Table 8 below details these findings.

TABLE 8

Summary of 50% responders after 12 weeks of treatment for all seizure sub-types

|  | Atonic seizures (n = 27) | Tonic seizures (n = 45) | Tonic-clonic seizures (n = 65) | Clonic seizures (n = 8) | Myoclonic seizures (n = 30) | Absence seizures (n = 28) |
| --- | --- | --- | --- | --- | --- | --- |
| >50% reduction in seizures | 63% (n = 17) | 49% (n = 22) | 43% (n = 28) | 50% (n = 4) | 43% (n = 13) | 64% (n = 18) |
| <50% reduction in seizures | 37% (n = 10) | 51% (n = 23) | 37% (n = 37) | 50% (n = 4) | 57% (n = 17) | 36% (n = 10) |

From Table 8 it can be seen that when the number of atonic seizures recorded is compared with other generalised seizure types such as tonic seizures (49% of patients experienced a greater than 50% reduction in seizure), tonic-clonic seizures (43% of patients experienced a greater than 50% reduction in seizure), and myoclonic seizures (43% of patients experienced a greater than 50% reduction in seizure) the fact that nearly two thirds (63%) of patients experiencing atonic seizures had a greater than 50% reduction in the number of seizures that occurred is very surprising.

REFERENCES

Ames F R and Cridland S (1986). "Anticonvulsant effects of cannabidiol." S Afr Med J 69:14.

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et. al. (1980). "Chronic administration of cannabidiol to healthy volunteers and epileptic patient." Pharmacology. 21:175-85

Dravet C. The core Dravet syndrome phenotype. Epilepsia. 2011 April; 52 Suppl 2:3-9.

Eadie, M J (December 2012). "Shortcomings in the current treatment of epilepsy." *Expert Review of Neurotherapeutics* 12 (12): 1419-27.

Geffrey A, Pollack S, Paolini J, Bruno P, Thiele E (2014) "Cannabidiol (CBD) treatment for refractory epilepsy in Tuberous Sclerosis Complex (TSC)." American Epilepsy Society Annual Meeting. 5-9 Dec. 2014.

Kwan P, Arzimanoglou A, Berg A T, Brodie M J, Hauser W A, Mathern G, Moshe S L, Perucca E, Wiebe S, French J. (2009) "Definition of drug resistant epilepsy: Consensus proposal by the ad hoc Task Force of the ILAE Commission on Therapeutic Strategies." Epilepsia.

Maa E and Figi P (2014). "The case for medical marijuana in epilepsy", Epilepsia 55(6):783-786

Mechoulam R and Carlini E A (1978). "Toward drugs derived from cannabis." Die naturwissenschaften 65:174-9.

Pelliccia A, Grassi G, Romano A, Crocchialo P (2005). "Treatment with CBD in oily solution of drug resistant paediatric epilepsies". Congress of Cannabis and the Cannabinoids, Leiden, The Netherlands. International Association for Cannabis as a Medicine. p 14.

Porter B E, Jacobson C (December 2013). "Report of a parent survey of cannabidiol-enriched cannabis use in paediatric treatment resistant epilepsy" Epilepsy Behaviour. 29(3) 574-7

Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." Epilepsia. 52 Suppl 7: 2-26

The invention claimed is:

1. A method of treating seizures in a patient with Lennox-Gastaut syndrome or Dravet syndrome, comprising orally administering to the patient in need thereof cannabidiol (CBD), wherein the CBD has a purity of at least 95% (w/w), and wherein the CBD is administered in a composition, comprising:
   (i) CBD at a concentration ranging from about 22.5 mg/mL and about 110 mg/mL;
   (ii) ethanol at a concentration ranging from about 71.1 mg/mL to about 86.9 mg/mL;
   (iii) a sweetener at a concentration ranging from about 0.45 mg/mL to about 0.55 mg/mL;
   (iv) flavoring at a concentration ranging from about 0.18 mg/mL to about 0.22 mg/mL;
   and (v) a solvent.

2. The method according to claim 1, wherein the sweetener is sucralose.

3. The method according to claim 1, wherein the flavoring is strawberry flavor.

4. The method according to claim 1, wherein the composition comprises from about 25 mg/mL to about 100 mg/mL of CBD.

5. The method of claim 1, wherein the composition comprises about 79 mg/mL of ethanol.

6. The method of claim 2, wherein the composition comprises about 0.5 mg/mL of sucralose.

7. The method of claim 3, wherein the composition comprises about 0.2 mg/mL of strawberry flavoring.

8. The method of claim 1, wherein the composition comprises about 100 mg/mL of CBD that has a purity of at least 98% (w/w).

9. The method of claim 1, wherein the composition comprises:
   (i) about 90 mg/mL to about 110 mg/mL of CBD that has a purity of at least 98% (w/w);
   (ii) about 71.1 mg/mL to about 86.9 mg/mL of ethanol;
   (iii) about 0.45 mg/mL to about 0.55 mg/mL of sucralose;
   (iv) about 0.18 mg/mL to about 0.22 mg/mL of strawberry flavoring; and
   (v) sesame oil q.s. to about 1.0 ml.

10. An oral pharmaceutical composition comprising: (i) cannabidiol (CBD) at a concentration of between about 22.5 mg/ml and about 110 mg/ml, (ii) ethanol at a concentration of about 71.1 mg/ml to about 86.9 mg/ml, (iii) sweetener at a concentration of about 0.45 mg/ml to about 0.55 mg/ml, (iv) flavoring at a concentration of about 0.18 mg/ml to about 0.22 mg/ml, and (v) sesame oil.

11. The oral pharmaceutical composition of claim 10, wherein the CBD is at a concentration of about 100 mg/mL±10%.

12. The oral pharmaceutical composition of claim 10, wherein the CBD has a purity of at least about 95% (w/w).

13. The oral pharmaceutical composition of claim 10, wherein the CBD has a purity of at least about 98% (w/w).

14. The oral pharmaceutical composition of claim 10, wherein the sweetener is sucralose.

15. The oral pharmaceutical composition of claim 10, wherein the flavoring is strawberry flavoring.

16. The oral pharmaceutical composition of claim 10, wherein: (i) the CBD is at a concentration of between about 90 mg/ml and about 110 mg/ml; (ii) ethanol is at a concentration of about 71.1 mg/ml to about 86.9 mg/mL; (iii) the sweetener is at a concentration of about 0.45 mg/ml to about 0.55 mg/ml; (iv) the flavoring is at a concentration of about 0.18 mg/ml to about 0.22 mg/ml; and (v) the sesame oil, q.s. to about 1.0 ml.

17. The composition of claim 16, wherein the CBD has a purity of at least about 95% (w/w).

18. The composition of claim 16, wherein the CBD has a purity of at least about 98% (w/w).

19. The method according to claim 1, wherein the solvent is sesame oil.

20. An oral pharmaceutical composition, comprising: (i) CBD at a concentration of between about 22.5 mg/ml and about 110 mg/ml, wherein the CBD has a purity of at least about 95% (w/w); (ii) ethanol is at a concentration of about 71.1 mg/ml to about 86.9 mg/mL; (iii) the sweetener is at a concentration of about 0.45 mg/ml to about 0.55 mg/ml; (iv) the flavoring is at a concentration of about 0.18 mg/ml to about 0.22 mg/ml; and (v) sesame oil.

21. The oral pharmaceutical composition of claim 19, wherein the composition comprises:
   (i) about 90 mg/mL to about 110 mg/mL of CBD that has a purity of at least 98% (w/w);
   (ii) about 71.1 mg/mL to about 86.9 mg/mL of ethanol;
   (iii) about 0.45 mg/mL to about 0.55 mg/mL of sucralose; and
   (iv) about 0.18 mg/mL to about 0.22 mg/mL of strawberry flavoring.

* * * * *

UNITED STATES PATENT AND TRADEMARK OFFICE
CERTIFICATE OF CORRECTION

| | | |
|---|---|---|
| PATENT NO. | : 10,966,939 B2 | Page 1 of 1 |
| APPLICATION NO. | : 16/911914 | |
| DATED | : April 6, 2021 | |
| INVENTOR(S) | : Guy et al. | |

It is certified that error appears in the above-identified patent and that said Letters Patent is hereby corrected as shown below:

Page 4, Item (56), Column 1, Line 42, replace "Life Sci. De. 1, 1973" with --Life Sci. Dec. 1, 1973--.

Claim 11, Column 14, Line 18, replace "mg/mL±10%" with --mg/mL ± 10%--.

Claim 21, Column 14, Line 49, replace "claim 19," with --claim 20,--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*